US00PP11262P

United States Patent [19]

Zary

[11] Patent Number: Plant 11,262

[45] Date of Patent: Mar. 7, 2000

[54] FLORIBUNDA ROSE PLANT NAMED 'JACMEEN'

[75] Inventor: Keith W. Zary, Thousand Oaks, Calif.

[73] Assignee: Bear Creek Gardens, Inc., Medford, Oreg.

[21] Appl. No.: 09/000,600

[22] Filed: Dec. 30, 1997

[51] Int. Cl.[7] ..... A01H 5/00

[52] U.S. Cl. ..... Plt./150

[58] Field of Search ..... Plt./149, 150, 147, Plt./138, 136, 139, 106, 108

*Primary Examiner*—Howard J. Locker

*Attorney, Agent, or Firm*—Klarquist Sparkman Campbell Leigh & Whinston, LLP

[57] ABSTRACT

A floribunda rose plant having resistance to powdery mildew and rust; early flowering of large flowers presented in large, open clusters; and dark green, glossy foliage.

1 Drawing Sheet

The present invention relates to a new and distinct variety of rose plant of the floribunda class which was originated by me by crossing the variety 'JACdew', U.S. Plant Pat. No. 5,122, with the variety 'HARrooney', U.S. Plant Pat. No. 5,582.

The primary objective of this breeding was to produce a new rose variety having the resistance to powdery mildew and rust and the glossy foliage of the female parent combined with the quite large flowers, good cluster formation, and early flowering of the male parent. The objective was substantially achieved, along with other desirable improvements, as evidenced by the following unique combination of characteristics that are outstanding in the new variety and that distinguish it from its parents, as well as from all other varieties of which I am aware:

1. Dark green, glossy foliage;
2. Flowers produced in large open clusters;
3. Early flowering;
4. Large, individual flowers;
5. Resistance to rust and powdery mildew.

In Somis and Wasco, Calif. and in Medford, Oreg., 'JACmeen' came into bloom in the first ten percent of all seedlings in evaluation trials.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent.*—'JACdew' (U.S. Plant Pat. No. 5,122).

*Pollen parent.*—'HARrooney' (U.S. Plant Pat. No. 5,582).

Classification:

*Botanical.*—Rosa hybrida.

*Commercial.*—Floribunda.

FLOWER

Observations made from specimens grown in a garden environment at Somis, Calif. from January, 1996–August, 1997.

Blooming habit: Continuous.

Bud:

*Size.*—One and one-quarter inch long when the petals start to unfurl.

*Form.*—The bud form is long, pointed ovoid.

*Color.*—When sepals first divide, bud color is Orange-Red Group 34A. When half blown, the upper and lower sides of the petals are Red Group 43B.

*Sepals.*—Color: Green group 138B. Surface texture: Covered with fine hairs. There are three lightly appendaged sepals. There are two appendaged sepals with hairy edges.

*Receptacle.*—Color: Green Group 137C. Shape: Funnel. Size: Medium (5/16" long ×3/16" wide). Surface: Smooth.

*Peduncle.*—Length: Medium (2 to 2½"). Surface: Smooth. Color: Light green. Strength: Stiff, erect.

Bloom:

*Size.*—Large. Average open size is four to four and one-half inches.

*Borne.*—Several together in rounded clusters of three to seven flowers.

*Stems.*—Short (8–12").

*Form.*—When first open: High-centered. Permanence: Flattens, all petals curl.

*Petalage.*—Number of petals under normal conditions 20–25.

*Color.*—The upper sides of the petals are Red Group 43B. The reverse sides of the petals are Red Group 43B. The base of each petal has a small (3/16"×3/16") yellow half moon at the point of attachment. The major color on the upper side is Red Group 43B.

*Variegations.*—None.

*Discoloration.*—At the end of the first day: No change. At the end of the third day: No change. By day five or six there is a general fading to Red Group 43D followed by petal drop.

*Fragrance.*—Slight.

Petals:

*Texture.*—Thick.

*Shape.*—Round to slightly deltoid.

*Form.*—Tips slightly recurved.

*Arrangement.*—Imbricated. Petaloids in the center are few.

*Persistence.*—Drop off cleanly.

*Lastingness.*—On the plant: Fair (five or six days). As a cut flower: Not tested.

Reproductive parts:

*Anthers.*—Size: Medium. Quantity: Many. Color: Yellow. Arrangement: Regular around styles.

*Filaments*.—Color: Reddish-brown.
*Pollen*.—Color: Gold yellow.
*Styles*.—Color: Reddish.
*Stigmas*.—Color: Greenish-white.

Plant:
*Form*.—Bush.
*Growth*.—Very vigorous; upright; branching. Height after one full season of growth in Somis, Calif. is 3½' 4'; width 3'.

Foliage: Number of leaflets on normal mid-stem leaves: Five, sometimes seven.
*Size*.—Large (6"×4").
*Quantity*.—Abundant.
*Color*.—New foliage: Upper and lower surfaces, Greyed-Red Group 178A. Old foliage: Upper surface: Green Group 139A. Lower surface: Green Group 139C.
*Shape*.—Pointed oval.
*Texture*.—Upper side: Leathery, glossy.
*Edge*.—Serrated.
*Serration*.—Single, small.
*Petiole rachis*.—Color: Reddish.
*Petiole underside*.—Smooth with a few prickles.
*Stipules*.—Medium (½" long); serrated, bearded.
*Disease resistance*.—Resistant to mildew and rust under normal growing conditions at Somis, Calif.

Wood:
*New wood*.—Color: Reddish. Bark: Smooth.
*Old wood*.—Color: Green. Bark: Smooth.

Prickles:
*Quantity*.—On main canes from base: Many. On laterals from main canes: Many.
*Form*.—Medium (⅜"); hooked downward.
*Color when young*.—Red.

Small prickles:
*Quantity*.—On main stalks: None. On laterals: None.

I claim:

1. A new and distinct variety of rose plant of the floribunda class, substantially as herein shown and described, characterized particularly as to novelty by its resistance to powdery mildew and rust, large flowers that are presented in large, open clusters, early flowering; and dark green, glossy foliage.

* * * * *

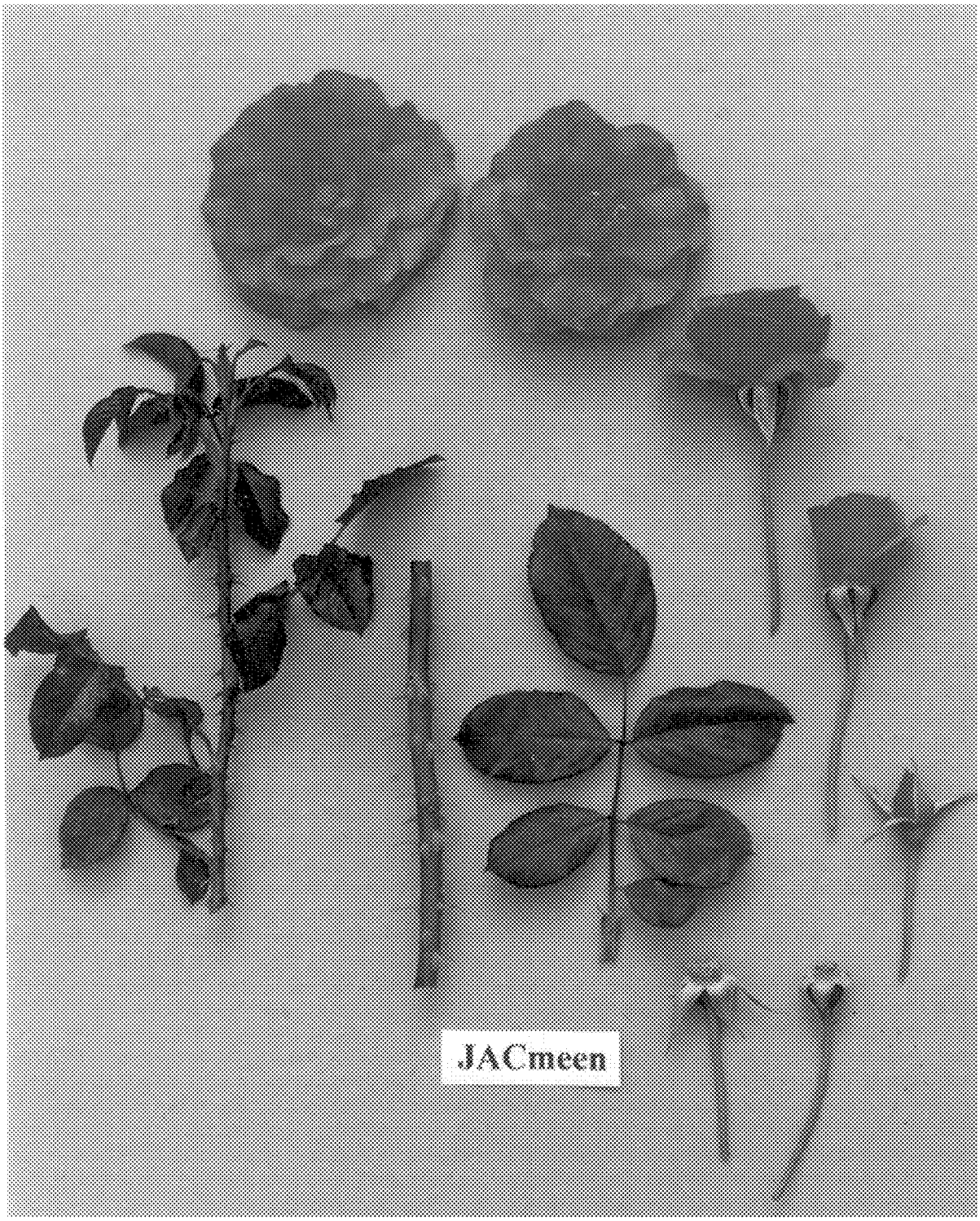
JACmeen

UNITED STATES PATENT AND TRADEMARK OFFICE

CERTIFICATE OF CORRECTION

PATENT NO. : PP 11,262
DATED : March 7, 2000
INVENTOR(S) : Keith W. Zary

It is certified that error appears in the above-identified patent and that said Letters Patent is hereby corrected as shown below:

Column 3,
Lines 8-9, change "3 ½'4';" to -- 3½'-4' --, as shown on Page 4, Line 29 of the Application.

Column 4,
Line 19, change "rust," to -- rust; --, as shown on Page 6, Line 7 of the Application.
Line 20, change "open clusters," to -- open clusters; --, as shown on Page 6, Line 8 of the Application.

Signed and Sealed this

Eleventh Day of December, 2001

*Attest:*

Nicholas P. Godici

NICHOLAS P. GODICI
*Acting Director of the United States Patent and Trademark Office*

*Attesting Officer*

UNITED STATES PATENT AND TRADEMARK OFFICE

CERTIFICATE OF CORRECTION

PATENT NO. : PP 11,262
DATED : March 7, 2000
INVENTOR(S) : Keith W. Zary

It is certified that error appears in the above-identified patent and that said Letters Patent is hereby corrected as shown below:

Column 3,
Lines 8-9, change "3 ½'4';" to -- 3½'-4' --, as shown on Page 4, Line 29 of the Application.

Column 4,
Line 19, change "rust," to -- rust; --, as shown on Page 6, Line 7 of the Application.
Line 20, change "open clusters," to -- open clusters; --, as shown on Page 6, Line 8 of the Application.

Signed and Sealed this

Eighteenth Day of December, 2001

*Attest:*

*Attesting Officer*

JAMES E. ROGAN
*Director of the United States Patent and Trademark Office*